United States Patent [19]

Berthold et al.

[11] 4,124,719

[45] Nov. 7, 1978

[54] 4-PHENYLHEXAHYDRO-4-INDOLINOL DERIVATIVES

[75] Inventors: Richard Berthold; Franz Troxler, both of Bottmingen, Switzerland

[73] Assignee: Sandoz Ltd., Basel, Switzerland

[21] Appl. No.: 790,416

[22] Filed: Apr. 25, 1977

Related U.S. Application Data

[63] Continuation-in-part of Ser. No. 637,313, Dec. 3, 1975, abandoned.

[30] Foreign Application Priority Data

May 7, 1976 [CH] Switzerland ........................ 5753/76
May 31, 1976 [CH] Switzerland ........................ 6782/76
Dec. 6, 1974 [CH] Switzerland ........................ 16236/74

[51] Int. Cl.$^2$ ................... A61K 31/40; A61K 31/405; C07D 209/08

[52] U.S. Cl. ........................ 424/274; 260/326.11 R; 542/429

[58] Field of Search ................ 260/326.11 R, 289 H, 260/240 R, 240 K; 424/274; 542/429

[56] References Cited

U.S. PATENT DOCUMENTS

| 2,858,314 | 10/1958 | Georgian .................... 260/326.11 R |
| 3,028,394 | 4/1962 | Popelak et al. ..................... 260/319 |

FOREIGN PATENT DOCUMENTS

2,552,563 6/1976 Fed. Rep. of Germany ... 260/326.11 R

*Primary Examiner*—Alton D. Rollins
*Attorney, Agent, or Firm*—Gerald D. Sharkin; Robert S. Honor; Thomas O. McGovern

[57] ABSTRACT

The invention provides new (3aRS,4SR,7aRS)-4-phenyl-hexahydro-4-indolinol derivatives useful as antidepressants and anti-arrhythmics.

66 Claims, No Drawings

4-PHENYLHEXAHYDRO-4-INDOLINOL DERIVATIVES

This is a continuation-in-part of our application Ser. No. 637,313 filed on Dec. 3, 1975, now abandoned.

The present invention relates to hexahydroindolinols.

The present invention provides compounds of formula I,

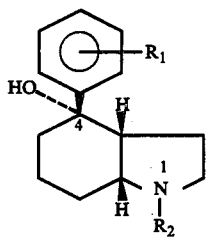

wherein
$R_1$ is hydrogen, alkyl of 1 to 4 carbon atoms, alkoxy of 1 to 4 carbon atoms, fluorine, chlorine or hydroxy, and $R_2$ is
(i) alkyl of 1 to 4 carbon atoms,
(ii) alkenyl or alkynyl of 3 to 7 carbon atoms, wherein the multiple bond is located in a position other than $\alpha$ to the nitrogen atom to which $R_2$ is bound,
(iii) cycloalkyl of 5 to 7 carbon atoms,
(iv) alkyl of 1 to 4 carbon atoms monosubstituted by cycloalkyl of 3 to 7 carbon atoms,
(v) hydroxyalkyl of 2 to 4 carbon atoms, wherein the hydroxy moiety is attached to a carbon atom other than a carbon atom $\alpha$ to the nitrogen atom to which $R_2$ is bound,
(vi) a group $-(CH_2)_p-CO-A$, where $p$ is a whole number from 1 to 3 and A is alkyl of 1 to 4 carbon atoms or alkoxy of 1 to 4 carbon atoms, or
(vii) a group

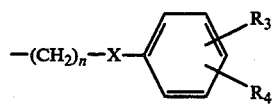

wherein $R_3$ and $R_4$, independently, are hydrogen, alkyl of 1 to 4 carbon atoms, alkoxy of 1 to 4 carbon atoms, or halogen, and either X is a direct bond, vinylene or carbonyl and $n$ is a whole number from 1 to 5 or X is $-O-$, $-S-$, $-SO-$, $-SO_2-$ or $-NR_5-$, wherein $R_5$ is hydrogen, phenyl, alkyl of 1 to 4 carbon atoms or alkanoyl of 2 to 4 carbon atoms, and $n$ is a whole number from 2 to 5, and compounds of formula I',

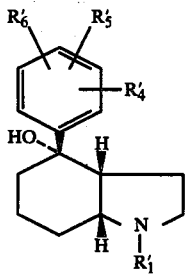

wherein $R_1'$ is hydrogen, alkyl of 1 to 4 carbon atoms, cycloalkyl of 5 or 6 carbon atoms, alkyl of 1 to 4 carbon atoms mono-substituted by cycloalkyl of 3 to 7 carbon atoms, alkenyl or alkynyl of 3 to 5 carbon atoms and wherein the multiple bond is other than in the $\alpha,\beta$-position, hydroxyalkyl of 2 to 5 carbon atoms wherein the hydroxy group is attached to other than the $\alpha$-carbon atom, or a radical of formula II',

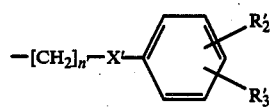

wherein
$R_2'$ and $R_3'$, independently, are hydrogen, alkyl of 1 to 4 carbon atoms, alkoxy of 1 to 4 carbon atoms, fluorine or chlorine, and either
(a) $n'$ is 1, 2 or 3, and X' is a single bond, methylene, vinylene or carbonyl, or (b) $n'$ is 2 or 3, and X' is oxygen or sulphur, and either
(i) $R_4'$ and $R_5'$, independently, are fluorine, chlorine, trifluoromethyl, alkyl of 1 to 4 carbon atoms, or alkoxy of 1 to 4 carbon atoms, and
$R_6'$ is hydrogen,
or
(ii) $R_4'$ and $R_5'$ are attached to adjacent ring carbon atoms, and, together, are $-(CH_2)_{m'}-$, wherein $m'$ is 3 or 4, $-CH=CH-CH=CH-$, or $-CH_2-CH=CH-$, and
$R_6'$ is hydrogen, fluorine, chlorine, trifluoromethyl, alkyl of 1 to 4 carbon atoms or alkoxy of 1 to 4 carbon atoms.

The compounds of formula I will now be described in more detail.

The alkyl and alkoxy moieties preferably have 1 to 2 carbon atoms, especially 1. $R_1$ preferably is hydrogen, alkyl, alkoxy, fluorine or chlorine. $R_2$ is preferably alkyl, alkenyl, hydroxyalkyl, $-(CH_2)_p-CO-A$ or

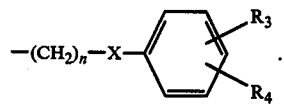

When $R_2$ is hydroxyalkyl, this preferably has 2 or 3 carbon atoms. The significance $p$ is preferably 2 or 3. When $R_2$ is cycloalkylalkyl, this is preferably cyclopropylmethyl.

A is preferably alkyl.

$R_3$ is preferably hydrogen, halogen or alkyl. $R_4$ is preferably hydrogen. When $R_3$ and/or $R_4$ is halogen, this is fluorine, chlorine or bromine, preferably fluorine or chlorine.

When X is a direct bond or vinylene, n is preferably a whole number from 1 to 4. When X is —O—, —S—, —SO—, —SO$_2$—, —CO— or —NR$_5$—, n is preferably 2 or 3. When R$_5$ is alkanoyl, this preferably has 2 or 3 carbon atoms.

X is preferably a direct bond, —CO—, —O—, —S—, —SO$_2$—, especially a direct bond or —CO—.

The present invention provides a process (a) for the production of a compound of formula I, as defined above, which comprises introducing a group R$_2$, as defined above, into the 1-position of a compound of formula II,

II wherein R$_1$ is as defined above, or (b) for the production of a compound of formula Ia, Ia wherein R$_1^I$ is hydrogen, alkyl or alkoxy of 1 to 4 carbon atoms, fluorine or chlorine, and E is hydrogen, alkyl of 1 to 3 carbon atoms, cycloalkyl of 3 to 7 carbon atoms, alkyl of 1 to 3 carbon atoms mono-substituted by cycloalkyl of 3 to 7 carbon atoms, or a group —(CH$_2$)$_m$—⟨Ar⟩(R$_3$)(R$_4$) , wherein m is a whole number from 0 to 4 and R$_3$ and R$_4$ are as defined above, which comprises reducing the -COD group to a —CH$_2$E group in a compound of formula III,

III wherein

R$_1^I$ is as defined above, and

D is alkoxy of 1 to 4 carbon atoms or

E, as defined above.

Processes (a) and (b) may be effected in analogous manner to known methods.

Process a) may be effected in conventional manner, e.g. for the alkylation of a secondary amine. For example as alkylating agent a compound of formula V, $$R_2—Y \qquad V$$

wherein

R$_2$ is as defined above, and

Y is a group capable of leaving under SN$_2$ conditions, may be used. Other known alkylating agents may be used, for example those mentioned hereinafter.

Y is conveniently an acid radical of a reactive ester, e.g. a halide such as a chloride, bromide or iodide, preferably a chloride or bromide, or an acid radical of an organic sulphonic acid, e.g. alkylsulphonyloxy, such as methylsulphonyloxy, or arylsulphonyloxy such as phenylsulphonyloxy or p-tolylsulphonyloxy.

The alkylation is conveniently effected in an organic solvent, for example in a solvent which is an amide of an aliphatic carboxylic acid, such as dimethyl formamide or in an aromatic hydrocarbon solvent, such as toluene. Preferably a basic condensation agent, e.g. an alkaline metal carbonate, such as potassium carbonate is present. The reaction temperature may be from room temperature to about 120° C.; preferably it is the reflux temperature.

Alternatively other known alkylating agents may be used, e.g. a compound obtainable from a compound of formula V, as defined above, by splitting off HY. For the production of compounds of formula I wherein R$_2$ is —(CH$_2$)$_2$.CO.A or —(CH$_2$)$_2$.CO—⟨Ar⟩(R$_3$)(R$_4$) , wherein A, R$_3$ and R$_4$ are as defined above, $\alpha,\beta$ unsaturated carbonyl compounds may be used. For example methyl vinyl ketone or an appropriate alkyl ester of acrylic acid may be used. Conveniently a suitable organic solvent is present, e.g. ethyl acetate or a lower alcohol such as methanol, ethanol. Conveniently the reaction mixture is stirred. The reaction temperature may vary from room temperature to the reflux temperature; preferably it is from 20° to 80° C.

Alternatively a 1,2-alkylene oxide may be used to produce a compound of formula I, wherein R$_2$ is 2-hydroxyalkyl. The reaction may be carried out under conventional conditions, e.g. a reaction temperature of from −10° to 100° C. may be used.

It will be appreciated that those significances of $R_2$ which contain a moiety which is not completely inert under the conditions of process a) may be introduced using an alkylating agent having the moiety in protected form and then the protecting group is split off. Thus one can produce particularly conveniently compounds of formula Ib,

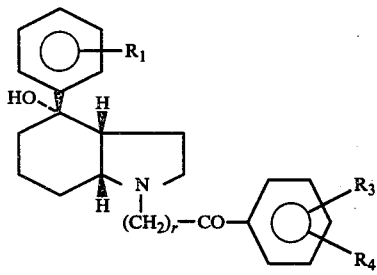

wherein $R_1$, $R_3$ and $R_4$ are as defined above, and r is a whole number from 1 to 5, by using in the above described alkylation processes alkylating agents capable of introducing a moiety of formula

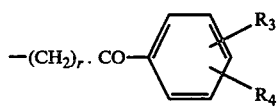

wherein $R_3$, $R_4$ and r are as defined above, wherein the carbonyl group is in ketal protected form to produce a compound with the carbonyl group in ketal protected form, e.g. the compound of formula VI,

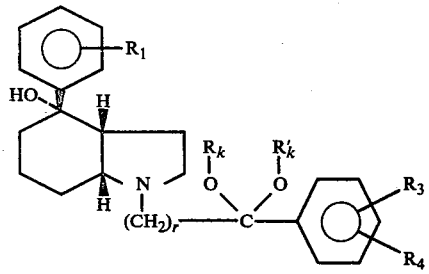

wherein $R_1$, $R_3$, $R_4$ and r are as defined above, and $R_k$ and $R_k'$ are independently alkyl of 1 to 4 carbon atoms, or together an alkyl chain of 2 to 4 carbon atoms, and then removing the protecting group or groups present to produce the compound of formula Ib with the carbonyl group in free form.

In an alternative variant, a reductive alkylation using the appropriate aldehyde or ketone may be used to produce compounds of formula I, wherein $R_2$ has an α-carbon atom carrying a hydrogen atom and wherein the moieties attached to the α-carbon are suitably inert under the conditions of a reductive alkylation. This variant may be effected in conventional manner, e.g. hydrogenolytically or according to the Leuckart-Wallach method.

Process b) may be effected in conventional manner for such reductions, e.g. for the reduction of a tert. amide or an N,N-disubstituted-urethane to a tert. amine. As reducing agent a metal or metalloid hydride, conveniently in complexed form may be used, for example diborane or the aluminium hydrides, such as aluminium hydride, dialkylaluminium hydride, lithiumaluminium hydride or a mixture of lithium aluminium hydride and aluminium chloride.

Conveniently an inert solvent is used, e.g. cyclic or open-chain ethers, such as diethyl ether and tetrahydrofuran.

The reaction temperature may be from about room temperature to about 100° C., for example from about 30° C. up to the reflux temperature. Reduction of tert.-amides is conveniently effected at from 40° to 60° C.; whereas the reduction of urethanes is conveniently effected at the reflux temperature.

It will be appreciated that when a chlorine or a bromine substituent is present in the compound of formula III aluminium hydride, dialkyl aluminium hydride, or diborane is conveniently used.

Preferred variants of process b) include the reduction of a compound of formula III wherein -COD is alkyloxycarbonyl, to produce a corresponding compound of formula Ia, wherein —$CH_2E$ is methyl. Process b) is also particularly suitable for the production of compounds of formula Ia, wherein —$CH_2E$ is cyclopropylmethyl.

Free base forms of compounds of formula I may be converted into acid addition salt forms in conventional manner and vice versa. Suitable acids include naphthalene-1,5-disulphonic acid, malonic acid, fumaric acid, hydrochloric acid and maleic acid.

The compounds of formulae II and III are new and may be produced in analogous manner to known methods. For example compounds of formula IIa,

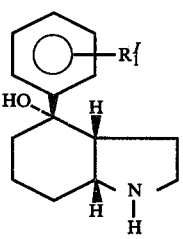

wherein $R_1^I$ is as defined above, may be produced by splitting off the alkoxycarbonyl group present in the 1-position of a compound of formula IIIa,

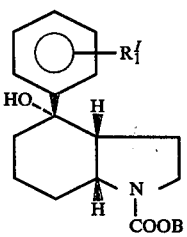

wherein $R_1^I$ is as defined above, and B is alkyl of 1 to 4 carbon atoms.

A compound of formula II, wherein $R_1$ is hydroxy may be produced by splitting the ether group of a compound of formula IIa, wherein $R_1^I$ is alkoxy of 1 to 4 carbon atoms. A suitable agent for splitting the ether group is a Lewis acid or a mixture of an alkali metal hydride and a mercaptan such as sodium hydride/methyl mercaptan.

A compound of formula IIIa as defined above may be produced by means of a Grignard Synthesis from a compound of formula IV,

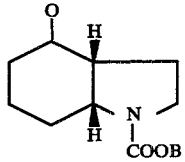

wherein B is as defined above, which proceeds in general stereospecifically.

Compounds of formula IV, wherein B is ethyl are known. Other compounds of formula IV may be prepared in analogous manner to known processes.

Compounds of formula III, wherein D is E as defined above, may be produced by N-acylating or N-formylating the corresponding compounds of formula II as defined above.

Insofar as the production of any starting material is not particularly described these compounds are known, or may be produced and purified in accordance with known processes, or in a manner analogous to processes described herein, e.g. in the Examples, or to known processes.

In the following Examples all temperatures are in degrees Centigrade, and are uncorrected.

EXAMPLE 1

(3aRS, 4SR, 7aRS)-Hexahydro-1-phenethyl-4-phenyl-4-indolinol [process variant a)]

14.8 g of (3aRS, 4SR, 7aRS)-hexahydro-4-phenyl-4-indolinol, 18.9 g of phenethyl bromide and 18 g of potassium carbonate in 170 ml of dimethylformamide were heated at reflux for 15 hours. After cooling, the reaction mixture was concentrated by evaporation and the concentrate was partitioned between water and ethyl acetate. The organic extract was dried over sodium sulphate, filtered, and concentrated to afford the title compound (M.P. of the hydrogen malonate from ethanol/ethyl acetate 133°-135°).

The starting material was produced as follows: a) Phenylmagnesium bromide (produced from 40 g of bromobenzene and 5 g of magnesium) was reacted with 30 g of cis-hexahydro-4-oxo-1-indoline carboxylic acid ethyl ester in tetrahydrofuran. After the reaction mixture had been stirred for 4 hours at room temperature, 100 ml of 2N hydrochloric acid and 200 ml diethyl ether were added. The organic phase was separated off, washed with water and dried over sodium sulphate. (3aRS, 4SR, 7aRS)-hexahydro-4-hydroxy-4-phenyl-1-indoline carboxylic acid ethyl ester remained as an oil after concentration by evaporation.

(b) To 30 g of (3aRS, 4SR, 7aRS)-hexahydro-4-hydroxy-4-phenyl-1-indoline carboxylic acid ethyl ester in 300 ml of methanol, 300 ml of 2N sodium hydroxide was added and the mixture was stirred overnight under reflux. After cooling the mixture was exhaustively extracted with methylene chloride. The organic extracts were extracted with 2N tartaric acid solution. The tartaric acid extract was made alkaline and extracted with methylene chloride. After working up the organic phase in conventional manner, (3aRS, 4SR, 7aRS)-hexahydro-4-phenyl-4-indolinol was obtained (M.P. of the hydrogen naphthalene-1,5-disulphonate from ethanol 228°-230°).

EXAMPLE 2

(3aRS, 4SR, 7aRS)-p-fluoro-4-[hexahydro-4-hydroxy-4-m-methoxyphenyl-1-indolinyl] butyrophenone (process variant a)

6 g of (3aRS, 4SR, 7aRS)-hexahydro-4-m-methoxyphenyl-4-indolinol and 3 g of 2-(3-choropropyl)-2-p-fluorophenyl-1,3-dioxolane were heated at 150° for 1 hour. After cooling, the solidified residue containing {(3aRS, 4SR, 7aRS)-1-[3-(2-p-fluorophenyl-1,3-dioxolan-2-yl)propyl]-4-m-methoxyphenyl-4-indolino}was made alkaline with 2N sodium hydroxide and the mixture was exhaustively extracted with methylene chloride. After working up in conventional manner, an oily residue was obtained which was dissolved in 165 ml of acetone. 16.5 ml of 2N hydrochloric acid was added and the mixture was maintained at room temperature for 48 hours. After concentration to dryness, the title compound was obtained as the hydrochloride (M.P. 168°-170° from acetone/diethyl ether).

EXAMPLE 3

(3aRS, 4SR, 7aRS)-4-p-chlorophenyl-hexahydro-1-methyl-4-indolinol [process variant b)]

15 g of (3aRS, 4SR, 7aRS)-4-p-chlorophenyl-hexahydro-4-hydroxy-1-indoline carboxylic acid ethyl ester and 4 g of lithium aluminum hydride in 100 ml of tetrahydrofuran were heated at reflux for 15 hours. Any remaining lithium aluminum hydride was destroyed by the addition of water. Partition between water and diethyl ether afforded after separation and working up of the organic phase the title compound as an oil (M.P. of the face base from diethyl ether/petroleum ether 98°-101°).

EXAMPLE 4

(3aRS, 4SR, 7aRS)-4-p-chlorophenyl-1-cyclopropylmethyl-hexahydro-4-indolinol [process variant b)]

A solution of 5.2 g (3aRS, 4SR, 7aRS)-4-p-chlorophenyl-1-cyclopropylcarbonyl-hexahydro-4-indolinol in 300 ml of tetrahydrofuran was produced by warming, and was added to a suspension of 1.3 g of lithium aluminium hydride in 30 ml of tetrahydrofuran. The mixture was stirred at 50° for 30 minutes. A saturated solution of amonium sulphate was added. The mixture was filtered. The filtrate was concentrated and reacted with a concentrated solution of naphthalene-1,5-disulphonic acid. Diethyl ether was added, and bis-[(3aRS, 4SR, 7aRS)-4-p-chlorophenyl-1-cyclopropylmethyl-hexahydro-4-indolinol]naphthalene-1,5-disulphonate (M.P. 240°-242°).

The starting material was produced as follows: 2.74 g of Cyclopropanecarboxylic acid chloride was added dropwise to a solution of 7.2 g of (3aRS, 4SR, 7aRS)-4-p-chlorophenylhexahydro-4-indolinol and 2.5 ml of pyridine in 30 ml of methylene chloride at 0° to 10°. The mixture was stirred at room temperature for 1 hour, and then was washed first with a 10% tartaric acid solution, then with a sodium bicarbonate solution, then with a saturated salt solution. The organic phase was dried over sodium sulphate and concentrated to afford (3aRS, 4SR, 7aRS)-4-p-chlorophenyl-1-cyclopropylcarbonyl-hexahydro-4-indolinol. (M.P. 167°–169°).

The compounds of formula I listed in the Table below are also obtained.

| Example No. | R₁ | R₂ | | M.P. |
|---|---|---|---|---|
| *α) Using process a) analogous to Example 1:* | | | | |
| 5 | m-OCH₃ | —CH₂—CH=CH₂ | ns | 140–144° |
| 6 | p-F | —(CH₂)₂—O—⌬ | hf | 162–163° |
| 7 | m-OCH₃ | —(CH₂)₃—S—⌬—Cl | ns | 210–212° |
| 8 | m-OCH₃ | —(CH₂)₃—SO₂—⌬—Cl | ns | 139–141° * |
| 9 | m-OCH₃ | —(CH₂)₂—CH=CH—⌬—F | b | 102–103° |
| 10 | p-Cl | —CH₂—CH=CH₂ | ns | 120–122° |
| 11 | p-Cl | —CH₂—C≡CH | b | 92–94° |
| 12 | p-Cl | —(CH₂)₂—OH | ns | 233–235° |
| 13 | m-OCH₃ | —(CH₂)₃—O—⌬ | ns | 236–237° * |
| 14 | m-OCH₃ | —(CH₂)₃—COCH₃ | ns | 130° |
| 15 | p-Cl | —CH₂COCH₃ | b | 90–92° |
| 16 | m-OCH₃ | —(CH₂)₃—CO—⌬—F | hcl | 168–170° |
| 17 | p-Cl | —CH₂—△ | ns | 240–242° |
| 18 | p-Cl | —CH₂—CH=CH—⌬ | b | 80–82° |
| 19 | H | —(CH₂)₂—O—⌬(Cl,Cl) | | |
| *Using process a) analogous to Ex. 1 and 2:* | | | | |
| 20 | m-OCH₃ | —(CH₂)₃—CO—⌬—Cl | b | 97–99° |
| 21 | m-OCH₃ | —(CH₂)₃—CO—⌬ | ns | 237–239° |
| 22 | p-Cl | —(CH₂)₃—CO—⌬—F | hcl | 224–226° |
| 23 | m-OCH₃ | —CH₂—CO—⌬ | b | 125–126° |
| 24 | m-OCH₃ | —(CH₂)₃—CO—⌬(CH₃,CH₃) | ns | 196–198° |
| 25 | m-OCH₃ | —(CH₂)₃—CO—⌬—OCH₃ | ns | 206–208° |
| 26 | H | —(CH₂)₃—CO—⌬(OCH₃,OCH₃) | | |
| *γ) Using process a) analogous to Ex. 1 and process b) analogous to Example 4^(ii):* | | | | |
| 27 | m-OCH₃ | —(CH₂)₂—⌬ | b | 102–104° |
| 28 | p-Cl | —CH₃ | b | 98–101° |
| 29 | m-OCH₃ | —CH₂—⌬ | hf | 173° |
| 30 | H | —(CH₂)₃—⌬ | ns | 211–213° |
| 31 | m-OCH₃ | —(CH₂)₃—⌬ | ns | 240–241° |

-continued

| Example No. | $R_1$ | $R_2$ | | M.P. |
|---|---|---|---|---|
| 32 | p-Cl | $-(CH_2)_2-\phi$ | b | 105–107° |
| 33 | m-OCH$_3$ | $-(CH_2)_4-\phi$ | hme | 142–144° |
| 34 | p-Cl | $-CH_2-\text{cyclopentyl}$ | b | 92–94° |
| 35 | H | $-(CH_2)_2-\text{(3,4-dimethoxyphenyl)}$ | | |
| 36 | p-OCH$_3$ | $-(CH_2)_2-\phi$ | | |

δ) Using process a) analogous to Example 1 and process b) analogous to Examples 3[i)] and 4[i)]:

| 37 | m-OCH$_3$ | —CH$_3$ | hf | 156–158° |
| 38 | H | —CH$_3$ | ns | 229–231° |
| 39 | p-F | —CH$_3$ | hf | 159–161° |
| 40 | p-CH$_3$ | —CH$_3$ | hf | 130°* |
| 41 | o-CH$_3$ | —CH$_3$ | hf | 121–123° |
| 42 | p-OCH$_3$ | —CH$_3$ | | |
| 43 | o-Cl | —CH$_3$ | | |

ε) Using process b) and analogous to Example 4[ii)]:

| 44 | H | $-(CH_2)_2-\phi$ | hmo | 133–135° |

In the table:
* = decomposition.
ns = bis [base] naphthalene-1,5-disulphonate
nf = hydrogen fumarate
b = base
hmo = hydrogen malonate
hcl = hydrochloride
hme = hydrogen maleate
[i)] from corresponding compounds of formula III wherein D is ethoxy
[ii)] from corresponding compounds of formula III wherein D is E as defined above.

There are also obtained the following compounds of formula I,

| | $R_1$ | $R_2$ |
|---|---|---|
| a) | m-OH | $-(CH_2)_5-\text{C(=O)}-\text{C}_6\text{H}_3(O^nPr)_2$ |
| b) | m-O$^{iso}$Pr | $-CH(CH_2)_6$ |
| c) | m-O$^{iso}$Pr | $-(CH_2)_3 \cdot CO \cdot O^{iso}Pr$ |
| d) | m-O$^{iso}$Pr | $-(CH_2)_5-\text{C(=O)}-\text{C}_6\text{H}_3(^nBu)_2$ |
| e) | m-O$^{iso}$Pr | $-(CH_2)_5-\text{S(=O)}-\text{C}_6\text{H}_3(O^nBu)_2$ |
| f) | m-O$^{iso}$Pr | $-(CH_2)_5 \cdot NH-\text{C}_6\text{H}_3(O^nBu)_2$ |
| g) | m-O$^{iso}$Pr | $-(CH_2)_5-N(C_6H_5)-\text{C}_6\text{H}_3(O^nBu)_2$ |
| h) | m-O$^{iso}$Pr | $-(CH_2)_5-N(^{iso}Pr)-\text{C}_6\text{H}_3(O^nBu)_2$ |
| i) | m-O$^{iso}$Pr | $-(CH_2)_5-N(C(=O)Et)-\text{C}_6\text{H}_3(O^nBu)_2$ |
| j) | m-O$^{iso}$Pr | $-(CH_2)_2 \cdot CH(CH_3) \cdot CH=CH \cdot CH_3$ |
| k) | m-O$^{iso}$Pr | $-(CH_2) \cdot CH(CH_3) \cdot C\equiv C \cdot CH_2 \cdot CH_3$ |

The following compounds of formula I are also produced according to Example 1, 3 or 4:

| Example No. | $R_1$ | $R_2$ | M. Pt. | Production |
|---|---|---|---|---|
| 1" | 3-Cl | —CH$_3$ | 181–3°[1)] | 1 or 3 |
| 2" | 3-Cl | $-CH_2CH_2-\phi$ | 176–9°[1)] | 1 or 4 |
| 3" | 3-Cl | $-CH_2CH_2OH$ | 143–5°[1)] | 1 |
| 4" | H | $-CH_2-\text{(2,3-dichlorophenyl)}$ | 121–3°[2)] | 1 or 3 |
| 5" | 4-OH | —CH$_3$ | 178–9°[2)] | 1 or 3 |

[1)] hydrogen maleate
[2)] free base

The compounds of formula I are useful because they possess pharmacological activity in animals. In particular, the compounds of formula I are useful as antiarrhythmics, e.g. for the treatment of heart rhythm disorders, as indicated in standard tests, e.g. by a prolongation of the functional refractory period of the isolated albino guinea pig left atria according to the method of N. Reuter, e. Heeg and U. Haller [Arch. Pharmacol., 268, 323–333, (1971)], using concentrations of from 1 to 30 μ M.

For the above mentioned use the dosage will, of course, vary depending on he compound employed, mode of administration and therapy desired. However, in general, satisfactory results are obtained when administered at a daily dosage of from 0.01 mg to about 30 mg per kg animal body weight, conveniently given in divided doses 2 to 4 times a day or in sustained release form. For the larger mammal, the total daily dosage is in the range from about 1 to about 100 mg, and dosage forms suitable for oral administration comprise from about 0.2 mg to about 50 mg of the compounds admixed with a solid or liquid pharmaceutical carrier or diluent.

Preferred compounds have $R_1$ hydrogen, 3-methoxy, 4-methyl, 4-fluorine or 4-chlorine. Preferably $R_2$ is methyl, allyl, a group $—(CH_2)_p.CO.CH_3$, wherein p is as defined above, phenylalkyl of 7 to 10 carbon atoms, phenoxyalkyl with 8 - 9 carbon atoms, 3-p-chlorophenylthiopropyl, 3-p-chlorophenylthiopropyl, 3-p-chlorophenylsulphonylpropyl or a group

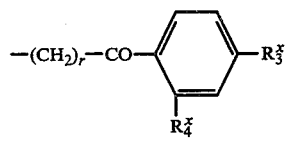

wherein
r is as defined above,
$R_3^x$ is hydrogen, fluorine, chlorine or methyl, and
$R_4^x$ hydrogen or methyl.

The Example 1 compound is the most interesting compound.

The compound of formula I are furthermore useful as anti-depressant agents, e.g. for the treatment of exogenous and endogenous depressions, as indicated in standard tests.

For example in one standard test in accordance with the method of G. Stille [Arz. Forsch. 14, 534–7 (1964)] an antagonism of the ptosis and catalepsy induced in rats by tetrabenazine is observed, on i.p. administration of from 5 to 50 mg/kg animal body weight of the compounds.

For the above mentioned use the dosage will, of course, vary depending on the compound employed, mode of administration and therapy desired. However, in general, satisfactory results are obtained when administered at a daily dosage of from 5 mg to about 50 mg per kg animal body weight, conveniently given in divided doses 2 to 4 times a day or in sustained release form. For the larger mammal, the total daily dosage is in the range from about 5 to about 300 mg, and dosage forms suitable for oral administration comprise from about 1 mg to about 150 mg of the compounds admixed with a solid or liquid pharmaceutical carrier or diluent.

For the anti-depressant use $R_1$ preferably is 4-chlorine. Preferably $R_2$ is methyl, allyl or 2-hydroxyalkyl.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

In one group of compounds X is —O—. In other group X is —S—. In another group X is —SO—. In another group X is —SO$_2$—. In another group X is NR$_5$. In a sub-group R$_5$ is phenyl. In another group X is a direct bond. In another group X is vinylene. In another group X is —CO—.

In one group A is alkoxy. In another group $R_2$ is cycloalkyl. In another group $R_2$ is alkenyl or alkynyl, e.g. of up to 5 carbon atoms.

The compounds of formula I' will now be described in detail:

In the above formula I', all alkyl and alkoxy moieties, except where otherwise stated, have preferably 2 carbon atoms or especially 1 carbon atom.

$R_1'$ is preferably alkyl, hydroxyalkyl or a radical of formula II, as defined above.

When $R_1'$ is alkyl substituted by cycloalkyl, the cycloalkyl moiety preferably has 2, 5 or 6 carbon atoms, and the alkyl moiety preferably one carbon atom. A preferred example is cyclopropylmethyl. The multiple bond of the alkenyl or alkynyl group preferably is in $\beta,\gamma$ position. The alkenyl or alkynyl group preferably has 3 carbon atoms. Hydroxyalkyl preferably has 2 or 3 carbon atoms.

n' is preferably 2. X' is preferably a single bond. When X' is vinylene the hydrogen atoms thereof may be cis or trans to each other.

$R_2'$ is preferably hydrogen, fluorine or chlorine. $R_3'$ is preferably hydrogen. Preferably $R_4'$ and $R_5'$ are in the meta and para position relative to the indoline nucleus. $R_6'$ is preferably hydrogen, and $R_4'$ and $R_5'$, independently, are preferably chlorine. When $R_4'$ and $R_5'$ are together $—(CH_2)_m—$, $—CH=CH—CH=CH—$ or $—CH_2—CH=CH—$, they are preferably $—CH=CH—CH=CH—$ and/or $R_6'$ is preferably hydrogen, chlorine or fluorine, preferably hydrogen.

The present invention also provides a process for the production of a compound of formula I', as defined above, which comprises (a) for the production of a compound of formula I'a,

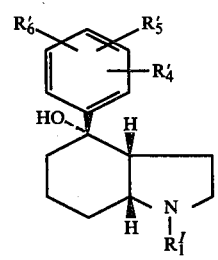

wherein
$R_1^I$ is $R_1$ as defined above with the proviso that it is other than hydrogen, and
$R_4'$, $R_5'$ and $R_6'$ are as defined above, introducing a group $R_1^I$ into the 1 position of a compound for formula Ib,

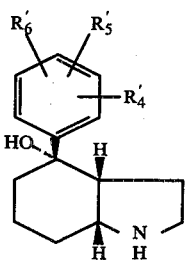

wherein $R_4'$, $R_5'$ and $R_6'$ are as defined above, (b) for the production of a compound of formula Ic,

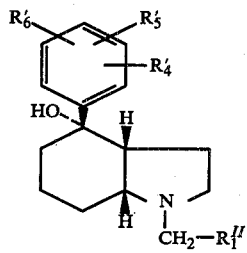

wherein
$R_1^{II}$ is hydrogen, alkyl of 1 to 3 carbon atoms, cycloalkyl of 3 to 7 carbon atoms, alkyl of 1 to 3 carbon atoms mono-substituted by cycloalkyl of 3 to 7 carbon atoms, or a radical of formula IIa',

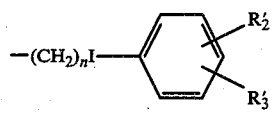

wherein $n^I$ is 0, 1 or 2, and $R_2'$ and $R_3'$ are as defined above, and $R_4'$, $R_5'$ and $R_6'$ are as defined above, reducing the group $R_7'$ to a group $-CH_2-R_1^{II}$ in a compound of formula II',

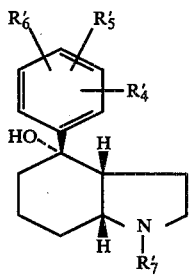

wherein
$R_4'$, $R_5'$ and $R_6'$ are as defined above, and $R_7'$ is a group capable of being reduced to methyl, or a group $COR_1^{III}$, wherein $R_1^{III}$ is as $R_1^{II}$, as defined above, with the proviso that it is other than hydrogen, or (c) for the production of a compound of formula Ib, as defined above, splitting off a group $R_8'$ from a compound of formula III',

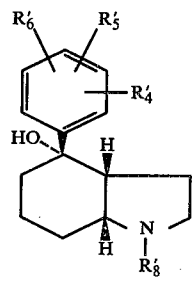

wherein
$R_4'$, and $R_6'$ are as defined above, and $R_8'$ is a group capable of being split off.

Process (a) may be effected in conventional manner for the alkylation of secondary amines.

For example, as alkylating agent there may be used the appropriate alkyl bromide or iodide. The reaction is conveniently effected in an aprotic solvent such as toluene or dimethylformamide. A basic condensation agent such as sodium carbonate is conveniently present. Suitable reaction temperatures are from about 10° to about 160° C., preferably boiling temperatures.

Alternatively, for production of compounds wherein X' is carbonyl and n' is 2 the corresponding compound of formula IV',

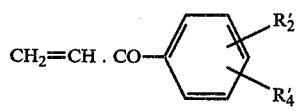

wherein $R_2'$ and $R_3'$ are as defined above, may be used in a Michael addition reaction, e.g. at from about 20° to about 80°.

Alternatively, for compounds of formula I, wherein $R_1$ is hydroxyalkyl, wherein the hydroxy group is attached to the β-carbon atom, the corresponding α, β-epoxide may be used as alkylating agent.

A reaction temperature of from about 10° to about 100° C. is suitable.

Process (b) may be effected in conventional manner for analogous reduction reactions, e.g. of analogous amides or urethanes to amines.

A suitable reducing agent is a complex metal hydride such as lithium aluminum hydride. When $R_7'$ is a group capable of being reduced to methyl, this may be formyl but is conveniently alkoxycarbonyl or arlyoxycarbonyl of up to 11 carbon atoms, especially ethoxycarbonyl. A suitable solvent is tetrahydrofuran. Suitable temperatures are from about 10° to about 100° C.

Process (c) may be effected in conventional manner for the splitting off of amine protecting groups, preferably under solvolytic conditions. $R_8'$ is for example alkoxycarbonyl or aryloxycarbonyl of up to 11 carbon atoms, especially ethoxycarbonyl. It is preferred to use alkaline conditions, e.g. sodium hydroxide, in methanol, ethanol or water.

Suitable temperatures are from about 10° to about 250° C., preferably about 100° C.

Compounds of formula II', wherein $R_7'$ is $COR_1^{II}$, alkoxycarbonyl or aryloxycarbonyl, may be produced by condensing a compound of formula Ib with the appropriate halide. Compounds of formula III', wherein $R_8'$ is alkoxycarbonyl or aryloxycarbonyl may be produced by a Grignard reaction between an appropriate Grignard reagent and a corresponding compound of formula V',

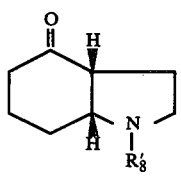

wherein $R_8'$ is as defined above.

Insofar as the preparation of any of the starting materials has not been particularly described, these compounds are known or may be produced and purified in accordance with known processes or in a manner analogous to processes described herein or known processes.

Free base forms of the compounds of formula I' may be converted into acid addition salt forms in conventional manner and vice versa. Suitable acids for salt formation include malonic acid and maleic acid.

In the following Examples all temperatures are in degrees Centigrade and are uncorrected.

EXAMPLE 1

(3aRS,4SR,7aRS)-4-(3,4-dichlorophenyl)hexahydro-1-(2-hydroxyethyl)-4-indolinol [process a)]

3.8 g (3aRS,4SR,7aRS)-4-(3,4-dichlorophenyl)hexahydro-4-indolinol (see Example 3), 1.6 g 2-bromoethanol and 4 g sodium carbonate are heated for 4 hours at 100° in 50 ml dimethylformamide. The resulting mixture is evaporated to dryness, and the residue is partitioned between methylene chloride and 2N tartaric acid. The aqueous phase is made alkaline and repeatedly extracted with methylene chloride. The last-mentioned methylene chloride phase is dried over sodium sulphate, and evaporated to yield as an oily residue, the title compound in crude free base form, which is converted by addition of an equivalent amount of malonic acid, into the hydrogen malonate. M.Pt. 161°.

EXAMPLE 2

(3aRS,4SR,7aRS)-4-(3,4-dichlorophenyl)hexahydro-1-methyl-4-indolinol [process b)]

28.5 g (3aRS,4SR,7aRS)-4-(3,4-dichlorophenyl)hexahydro-4-hydroxy-1-indoline carboxylic acid ethyl ester and 6.1 g lithium aluminium hydride in 200 ml tetrahydrofuran are refluxed for 2½ hours. Excess lithium aluminium hydride is decomposed by the addition of water to the cooled reaction mixture. The mixture is partitioned between water and ether. The organic phase is dried over magnesium sulphate and evaporated to yield the title material as an oil which is crystallized from ethanol. M.Pt. 69°–71°.

The title compound may also be produced in analogous manner to that disclosed in Example 1.

The starting material is obtained as follows:- 3,4-dichlorophenylmagnesium bromide (from 4.2 g magnesium and 38.5 g 1-bromo-3,4-dichlorobenzene) is treated with 26.4 g cis-perhydro-4-oxo-1-indoline-carboxylic acid ethyl ester in 300 ml tetrahydrofuran. The mixture is stirred for 4 hours, and then treated with 100 ml 2N hydrochloric acid and 200 ml ether. The organic phase is washed with water, dried over sodium sulphate, and evaporated to yield the starting material as an oil.

EXAMPLE 3

(3aRS,4SR,7aRS)-4-(3,4-dichlorophenyl)hexahydro-4-indolinol [process c)]

24.9 g (3aRS,4SR,7aRS)-4-(3,4-dichlorophenyl)hexahydro-1-indoline carboxylic acid ethyl ester in 240 ml methanol are treated with 240 ml 10N sodium hydroxide and refluxed for 15 hours. The cooled resulting mixture is repeatedly extracted with methylene chloride. The organic phase is extracted with 2N tartaric acid. The acidic phase is made alkaline and extracted with methylene chloride. The methylene chloride phases are dried over magnesium sulphate, and evaporated to give the title compound, in crude free base form, as an oil which is converted, by the addition of an equivalent amount of maleic acid, into the hydrogen maleate. M.Pt. 190°–191°.

In analogous manner the following compounds of formula I' may be produced, wherein:-

| Example No. | $R_1'$ | $R_4'$ | $R_5'$ | $R_6'$ | M.Pt. | Produced analogous to Example |
|---|---|---|---|---|---|---|
| 4 | —CH₃ | 3-CF₃ | 4-Cl | H | 140–142° [1] | 1 or 2 |
| 5 | —H | 3-CF₃ | 4-Cl | H | 141–144° [2] | 3 |
| 6 | —CH₃ | 2,3—CH=CH—CH=CH— | | H | 113–115° [3] | 1 or 2 |
| 7 | —CH₂—CH₂—C₆H₅ | 2,3—CH=CH—CH=CH— | | H | 178° [1][5] | 1 or 2 |
| 8 | —H | 2,3—CH=CH—CH=CH— | | H | oil | 3 |
| 9 | —CH₃ | 3,4—CH=CH—CH=CH— | | H | 134–135° [1] | 1 or 2 |
| 10 | —CH₂—CH₂—C₆H₅ | 3,4—CH=CH—CH=CH— | | H | 196–197° [2] | 1 or 2 |
| 11 | —H | 3,4—CH=CH—CH=CH— | | H | 202–204° [4] | 3 |

[1] hydrogen malonate
[2] hydrogen maleate
[3] free base
[4] hydrogen fumarate
[5] decomposition In analogous manner to that described in Example 1 the following compounds of formula I' may be produced, wherein:-

| Ex. | R'₁ | R₄ | R'₅ | R'₆ |
|---|---|---|---|---|
| (a) | cyclobutyl | 2-F | 3-O-n-C₃H₇ | H |
| (b) | —CH₂—cycloheptyl | 2-n-C₃H₇ | 4-O-n-C₃H₇ | H |
| (c) | —(CH₂)₅—cyclopropyl | 3-CF₃ | 5-CF₃ | H |
| (d) | —CH₂.CH₂.CH=CH.CH₂ | 3-CF₃ | 5-CF₃ | H |
| (e) | —CH₂.C≡CH | 3-CF₃ | 5-CF₃ | H |
| (f) | —(CH₂)₅OH | 3-CF₃ | 5-CF₃ | H |
| (g) | —CH₂—(phenyl with nC₃H₇ and OnC₃H₇) | 3-CF₃ | 5-CF₃ | H |
| (h) | —CH₂.CH₂.CH=CH—(phenyl with Cl, F) | 3,4-[CH₂]₄— | | 6-O-n-C₃H₇ |
| (i) | —CH₂.CH₂.CH₂.CO—(phenyl with Cl, nC₃H₇) | 2,3-[CH₂]₃— | | 4-F |
| (j) | —[CH₂]₄—(phenyl with Cl) | 3,4-CH₂—CH=CH— | | 5-nC₃H₇ |
| (k) | —[CH₂]₂—O—(phenyl with F) | 2,3-CH₂—CH=CH— | | 5-Cl |
| (l) | —[CH₂]₃—S—(phenyl with nC₃H₇) | 3,4-CH=CH—CH=CH— | | 2-CF₃ |

The compounds of formula I' are useful because they possess pharmacological activity in animals. In particular, the compounds of formula I are useful as antiarrhythmics, e.g. for the treatment of heart rhythm disorders, as indicated in standard tests, e.g. by a prolongation of the functional refractory period of the isolated albino guinea pig left atria according to the method of N. Reuter, E. Heeg and U. Haller [Arch. Pharmacol., 268, 323–333, (1971)], using concentrations of from 1 to 30 μ M.

For the above mentioned use the dosage will, of course, vary depending on the compound employed, mode of administration and therapy desired. However, in general, satisfactory results are obtained when administered at a daily dosage of from 0.01 mg to about 30 mg per kg animal body weight, conveniently given in divided doses 2 to 4 times a day or in sustained release form. For the larger mammal, the total daily dosage is in the range from about 1 to about 100 mg, and dosage forms suitable for oral administration comprise from about 0.2 mg to about 50 mg of the compounds admixed with a solid or liquid pharmaceutical carrier or diluent.

The compound of formula I' are furthermore useful as anti-depressant agents, e.g. for the treatment of exogenous and endogenous depressions, as indicated in standard tests.

For example in one standard test in accordance with the method of G. Stille [Arz. Forsch. 14, 534–7 (1964)] an antagonism of the ptosis and catalepsy induced in rats by tetrabenazine is observed, on i.p. administration of from 5 to 50 mg/kg animal body weight of the compounds.

For the above mentioned use the dosage will, of course, vary depending on the compound employed, mode of administration and therapy desired. However, in general, satisfactory results are obtained when administered at a daily dosage of from 5 mg to about 50 mg per kg animal body weight, conveniently given in divided doses 2 to 4 times a day or in sustained release form. For the larger mammal, the total daily dosage is in the range from about 5 to about 500 mg, preferably 5 to 300 mg, and the dosage forms suitable for oral administration comprise from about 1 mg to about 250 mg of the compounds admixed with a solid or liquid pharmaceutical carrier or diluent.

For the anti-depressant use it is preferred to have $R_1$ 2-hydroxyethyl or methyl.

The compounds of formula I' may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

In one group of compounds X' is —O—. In other group X' is —S—. In another group X' is a direct bond. In another group X' is vinylene. In another group X' is —CO—.

In one group $R_4'$, $R_5'$ and $R_6'$ are chosen from the significance (i) of formula I'.

In another group $R_4'$ and $R_5'$ together are —(CH$_2$)$_m$—.

In a further group $R_4'$ and $R_5'$ together are —CH═CH—CH═CH—.

In a further group $R_4'$ and $R_5'$ together are —CH$_2$—CH═CH—.

We claim:
1. A compound of formula I,

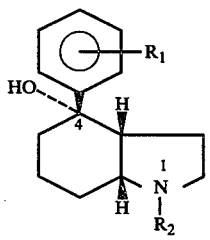

I wherein
$R_1$ is hydrogen, alkyl of 1 to 4 carbon atoms, alkoxy of 1 to 4 carbon atoms, fluorine, chlorine or hydroxy, and
$R_2$ is
(i) alkyl of 1 to 4 carbon atoms,
(ii) alkenyl or alkynyl of 3 to 7 carbon atoms, wherein the multiple bond is located in a position other than α to the nitrogen atom to which $R_2$ is bound,
(iii) cycloalkyl of 5 to 7 carbon atoms,
(iv) alkyl of 1 to 4 carbon atoms mono-substituted by cycloalkyl of 3 to 7 carbon atoms,
(v) hydroxyalkyl of 2 to 4 carbon atoms, wherein the hydroxy moiety is attached to a carbon atom other than a carbon atom α to the nitrogen atom to which $R_2$ is bound,
(vi) a group —(CH$_2$)$_p$—CO—A, wherein $p$ is a whole number from 1 to 3 and A is alkyl of 1 to 4 carbon atoms or alkoxy of 1 to 4 carbon atoms, or (vii) a group

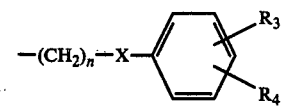

wherein $R_3$ and $R_4$, independently, are hydrogen, alkyl of 1 to 4 carbon atoms, alkoxy of 1 to 4 carbon atoms, or halogen, and either X is a direct bond, vinylene or carbonyl and $n$ is a whole number from 1 to 5 or X is —O—, —S—, —SO—, —SO$_2$— or —NR$_5$—, wherein $R_5$ is hydrogen, phenyl, alkyl of 1 to 4 carbon atoms or alkanoyl of 2 to 4 carbon atoms, and $n$ is a whole number from 2 to 5, or a pharmaceutically acceptable acid addition salt thereof.

2. A compound of claim 1,
wherein
$R_2$ is alkyl; alkenyl; alkynyl; cycloalkyl; cycloalkylmethyl of 4 to 8 carbon atoms; phenylalkyl of 7 to 11 carbon atoms; the phenyl ring being unsubstituted or monosubstituted by alkyl or alkoxy or halogen; a group —(CH$_2$)$_p$·CO·CH$_3$, wherein $p$ is a whole number from 1 to 3; a group

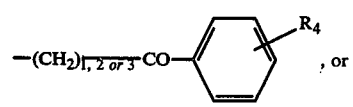, or

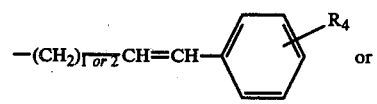 or

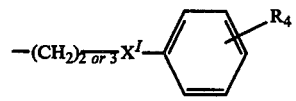

wherein
$X^I$ is —O—, —S—, —SO—, —SO$_2$— or —NR$_5$—, and
$R_4$ and $R_5$ are as defined in claim 1.

3. A compound of claim 2, wherein $R_2$ is alkyl, alkenyl, alkynyl, unsubstituted phenylalkyl of 7 to 11 carbon atoms, phenalkyl of 7 to 11 carbon atoms substituted by alkyl, alkoxy or halogen, —CH$_2$)$_2$ or $_3$·CO·CH$_3$ or

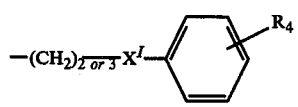

wherein
$X^I$ is —NR$_5$—,
$R_4$ is as defined in claim 2, and $R_5$ is alkyl.

4. A compound of claim 1, wherein $R_1$ is hydrogen, methoxy, fluorine, chlorine or methyl, and $R_2$ is allyl, methyl, or a group

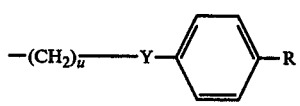

wherein
R is hydrogen, fluorine or chlorine, and either Y is a direct bond, —CO—, —O—, —S—, or —SO₂—, and
u is 2 or 3,
Y is vinylene and
u is 2.

5. A pharmaceutical composition useful in the treatment of depression, comprising an anti-depressant effective amount of a compound of claim 1 in association with a pharmaceutical carrier or diluent.

6. A method of treating depression which comprises administering to an animal in need of such treatment a therapeutically effective amount of a compound of claim 1.

7. A compound of formula II

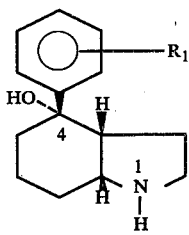

II wherein
R₁ is hydrogen, alkyl of 1 to 4 carbon atoms, alkoxy of 1 to 4 carbon atoms, fluorine, chlorine or hydroxy.

8. A compound of claim 1, wherein R₁ is hydrogen, alkyl, alkoxy, fluorine or chlorine.

9. A compound of claim 1, wherein R₂ is alkyl, alkenyl, hydroxyalkyl, —(CH₂)$_p$—CO—A, or

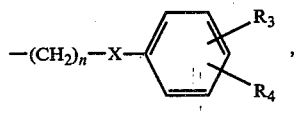

wherein p, A, n, X, R₃ and R₄ are as defined in claim 1.

10. A compound of claim 1, wherein X is a direct bond.

11. A compound of claim 1, wherein R₃ is hydrogen, halogen or alkyl.

12. A compound of claim 1, wherein R₄ is hydrogen.

13. A compound of claim 1, wherein R₁ and R₂ are respectively m-OCH₃ and —CH₂—CH=CH₂.

14. A compound of claim 1, wherein R₁ and R₂ are respectively p-F and

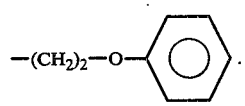

15. A compound of claim 1, wherein R₁ and R₂ are respectively m-OCH₃ and

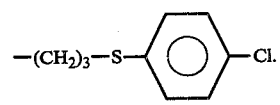

16. A compound of claim 1, wherein R₁ and R₂ are respectively m-OCH₃ and

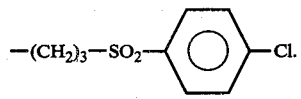

17. A compound of claim 1, wherein R₁ and R₂ are respectively m-OCH₃ and

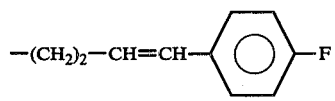

18. A compound of claim 1, wherein R₁ and R₂ are respectively p-Cl and —CH₂—CH=CH₂.

19. A compound of claim 1, wherein R₁ and R₂ are respectively p-Cl and —CH₂C≡CH.

20. A compound of claim 1, wherein R₁ and R₂ are respectively p-Cl and —(CH₂)₂—OH.

21. A compound of claim 1, wherein R₁ and R₂ are respectively m-OCH₃ and

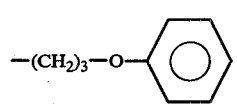

22. A compound of claim 1, wherein R₁ and R₂ are respectively m-OCH₃ and —(CH₂)₃—COCH₃.

23. A compound of claim 1, wherein R₁ and R₂ are respectively p-Cl and —CH₂COCH₃.

24. A compound of claim 1, wherein R₁ and R₂ are respectively m-OCH₃ and

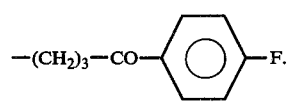

25. A compound of claim 1, wherein R₁ and R₂ are respectively p-Cl and

—CH₂—◁.

26. A compound of claim 1, wherein R₁ and R₂ are respectively p-Cl and

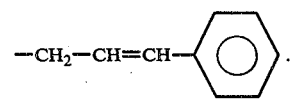

27. A compound of claim 1, wherein R₁ and R₂ are respectively H and

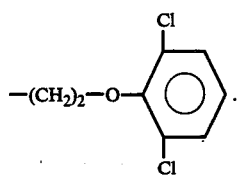

28. A compound of claim 1, wherein $R_1$ and $R_2$ are respectively m-OCH$_3$ and

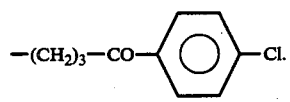

29. A compound of claim 1, wherein $R_1$ and $R_2$ are respectively m-OCH$_3$ and

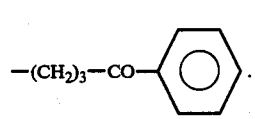

30. A compound of claim 1, wherein $R_1$ and $R_2$ are respectively p-Cl and

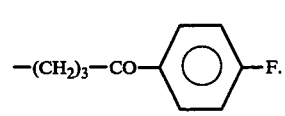

31. A compound of claim 1, wherein $R_1$ and $R_2$ are respectively m-OCH$_3$ and

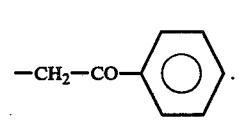

32. A compound of claim 1, wherein $R_1$ and $R_2$ are respectively m-OCH$_3$ and

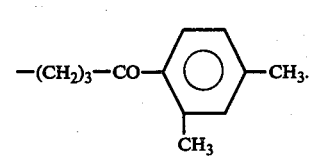

33. A compound of claim 1, wherein $R_1$ and $R_2$ are respectively m-OCH$_3$ and

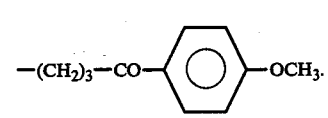

34. A compound of claim 1, wherein $R_1$ and $R_2$ are respectively H and

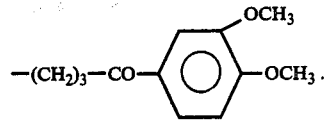

35. A compound of claim 1, wherein $R_1$ and $R_2$ are respectively m-OCH$_3$ and

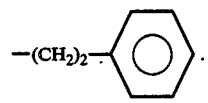

36. A compound of claim 1, wherein $R_1$ and $R_2$ are respectively p-Cl and —CH$_3$.

37. A compound of claim 1, wherein $R_1$ and $R_2$ are respectively m-OCH$_3$ and

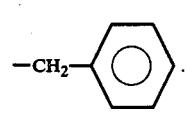

38. A compound of claim 1, wherein $R_1$ and $R_2$ are respectively H and

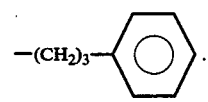

39. A compound of claim 1, wherein $R_1$ and $R_2$ are respectively m-OCH$_3$ and

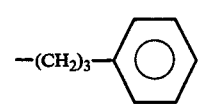

40. A compound of claim 1, wherein $R_1$ and $R_2$ are respectively p-Cl and

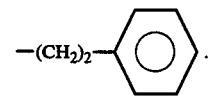

41. A compound of claim 1, wherein $R_1$ and $R_2$ are respectively m-OCH$_3$ and

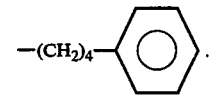

42. A compound of claim 1, wherein $R_1$ and $R_2$ are respectively p-Cl and

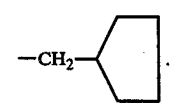

43. A compound of claim 1, wherein $R_1$ and $R_2$ are respectively H and

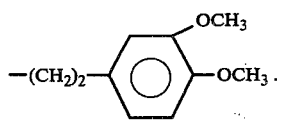

44. A compound of claim 1, wherein $R_1$ and $R_2$ are respectively p-$OCH_3$ and

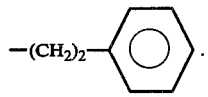

45. A compound of claim 1, wherein $R_1$ and $R_2$ are respectively m-$OCH_3$ and —$CH_3$.

46. A compound of claim 1, wherein $R_1$ and $R_2$ are respectively H and —$CH_3$.

47. A compound of claim 1, wherein $R_1$ and $R_2$ are respectively p-F and —$CH_3$.

48. A compound of claim 1, wherein $R_1$ and $R_2$ are respectively p-$CH_3$ and —$CH_3$.

49. A compound of claim 1, wherein $R_1$ and $R_2$ are respectively o-$CH_3$ and —$CH_3$.

50. A compound of claim 1, wherein $R_1$ and $R_2$ are respectively p-$OCH_3$ and —$CH_3$.

51. A compound of claim 1, wherein $R_1$ and $R_2$ are respectively o-Cl and —$CH_3$.

52. A compound of claim 1, wherein $R_1$ and $R_2$ are respectively H and

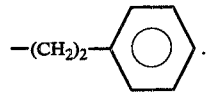

53. A compound of claim 1, wherein $R_1$ and $R_2$ are respectively 3-Cl and —$CH_3$.

54. A compound of claim 1, wherein $R_1$ and $R_2$ are respectively 3-Cl and

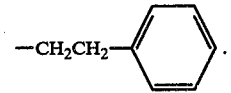

55. A compound of claim 1, wherein $R_1$ and $R_2$ are respectively 3-Cl and —$CH_2CH_2OH$.

56. A compound of claim 1, wherein $R_1$ and $R_2$ are respectively H and

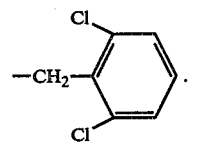

57. A compound of claim 1, wherein $R_1$ and $R_2$ are respectively 4-OH and —$CH_3$.

58. A compound of claim 2, wherein $R_2$ is alkyl, alkenyl, alkynyl, unsubstituted or substituted phenylalkyl, —$(CH_2)_2$ or $_3$·CO·$CH_3$ or

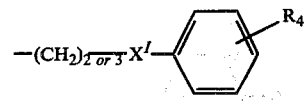

wherein
$X^I$ is —$NR_5$—, and $R_4$ and $R_5$ are as set out in claim 2.

59. A pharmaceutical composition useful in treating arrhythmia comprising an antiarrhythmic effective amount of a compound of claim 1 in association with a pharmaceutical carrier or diluent.

60. A pharmaceutical composition according to claim 59, comprising 0.2 to 50 milligrams of a compound of claim 1 per unit dosage.

61. A pharmaceutical composition according to claim 59 in which the compound is (3aRS, 4SR, 7aRS)-hexahydro-1-phenethyl-4-phenyl-4-indolinol.

62. A method of treating arrhythmia in animals which comprises administering to an animal in need of such treatment a therapeutically effective amount of a compound of claim 1.

63. A method according to claim 62 in which 1 to 100 milligrams of the compound are administered daily.

64. A method according to claim 62 in which 0.2 to 50 milligrams of the compound are administered per unit dose.

65. A method according to claim 62 in which the compound is (3aRS, 4SR, 7aRS)-hexahydro-1-phenethyl-4-phenyl-4-indolinol.

66. A compound of formula I',

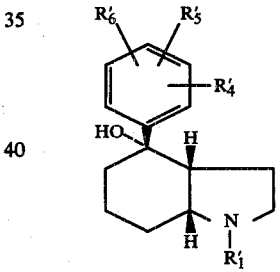

wherein $R_1'$ is hydrogen, alkyl of 1 to 4 carbon atoms, cycloalkyl of 5 or 6 carbon atoms, alkyl of 1 to 4 carbon atoms mono-substituted by cycloalkyl of 3 to 7 carbon atoms, alkenyl or alkynyl of 3 to 5 carbon atoms and wherein the multiple bond is other than in the $\alpha,\beta$-position, hydroxyalkyl of 2 to 5 carbon atoms wherein the hydroxy group is attached to other than the $\alpha$-carbon atom, or a radical of formula II',

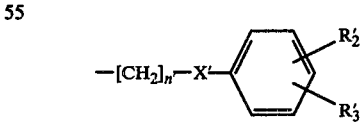

wherein
$R_2'$ and $R_3'$, independently, are hydrogen, alkyl of 1 to 4 carbon atoms, alkoxy of 1 to 4 carbon atoms, fluorine or chlorine, and
either
(a) $n'$ is 1, 2 or 3, and X' is a single bond, methylene, vinylene or carbonyl,
or (b) $n'$ is 2 or 3, and X' is oxygen or sulphur, and either
(i) $R_4'$ and $R_5'$, independently, are fluorine, chlorine, trifluoromethyl, alkyl of 1 to 4 carbon atoms, or alkoxy of 1 to 4 carbon atoms, and
$R_6'$ is hydrogen, or (ii) $R_4'$ and $R_5'$ are attached to adjacent ring carbon atoms, and, together, are $-(CH_2)_m-$, wherein $m$ is 3 or 4, $-CH=CH-CH=CH-$, or $-CH_2=CH-$, and
$R_6'$ is hydrogen, fluorine, chlorine, trifluoromethyl, alkyl of 1 to 4 carbon atoms or alkoxy of 1 to 4 carbon atoms, or a pharmaceutically acceptable acid addition salt thereof.

* * * * *